US009305759B2

(12) United States Patent
McEwen et al.

(10) Patent No.: US 9,305,759 B2
(45) Date of Patent: Apr. 5, 2016

(54) IONIZATION AT INTERMEDIATE PRESSURE FOR ATMOSPHERIC PRESSURE IONIZATION MASS SPECTROMETERS

(71) Applicant: UNIVERSITY OF THE SCIENCES IN PHILADELPHIA, Philadelphia, PA (US)

(72) Inventors: Charles Nehemiah McEwen, Newark (DE); Vincent Salvatore Pagnotti, Moosic, PA (US)

(73) Assignee: University of the Sciences in Philadelphia, Philadelphia, PA (US)

( * ) Notice: Subject to any disclaimer, the term of this patent is extended or adjusted under 35 U.S.C. 154(b) by 0 days.

(21) Appl. No.: 14/374,827

(22) PCT Filed: Jan. 24, 2013

(86) PCT No.: PCT/US2013/022883
§ 371 (c)(1),
(2) Date: Jul. 25, 2014

(87) PCT Pub. No.: WO2013/112680
PCT Pub. Date: Aug. 1, 2013

(65) Prior Publication Data
US 2014/0332695 A1 Nov. 13, 2014

Related U.S. Application Data

(60) Provisional application No. 61/591,049, filed on Jan. 26, 2012, provisional application No. 61/591,041, filed on Jan. 26, 2012, provisional application No. 61/642,871, filed on May 4, 2012, provisional application No. 61/691,029, filed on Aug. 20, 2012.

(51) Int. Cl.
*H01J 49/10* (2006.01)
*H01J 49/04* (2006.01)
(Continued)

(52) U.S. Cl.
CPC ............... *H01J 49/10* (2013.01); *G01N 30/72* (2013.01); *H01J 49/0404* (2013.01); *H01J 49/0495* (2013.01); *H01J 49/26* (2013.01)

(58) Field of Classification Search
CPC ... H01J 49/04; H01J 49/0404; H01J 49/0422; H01J 49/0445; H01J 49/0468; H01J 49/0495; H01J 49/10; H01J 49/107; H01J 49/16; H01J 49/168; H01J 49/24; G01N 30/72
USPC .......................................... 250/281, 282, 288
See application file for complete search history.

(56) References Cited

U.S. PATENT DOCUMENTS 4,209,696 A * 6/1980 Fite ........................ H01J 49/165
250/281
4,546,253 A * 10/1985 Tsuchiya et al. ............... 250/288
(Continued)

FOREIGN PATENT DOCUMENTS

JP 08-278286 A 10/1996
JP 11-108894 A 4/1999
(Continued)

*Primary Examiner* — Nicole Ippolito
*Assistant Examiner* — David E Smith
(74) *Attorney, Agent, or Firm* — Duane Morris LLP

(57) ABSTRACT

An ion source able to ionize liquid and gaseous effluents from interfaced liquid or gaseous separation techniques and from direct introduction of the analyte to the entrance of the ionization region. The liquid effluents from sources such as a liquid chromatograph are ionized by inlet ionization methods and the gaseous effluents from sources such as a gas chromatograph are ionized by a corona or Townsend electrical discharge, or an alpha or beta emitter, or by inlet ionization, or by photoionization. Ionization occurs in an intermediate pressure region linking atmospheric pressure and the vacuum of the mass analyzer. The source has the ability to ionize compounds from both liquid and gaseous sources, which facilitates ionization of volatile compounds separated by gas chromatography, volatile or non-volatile compounds separated by liquid chromatography, or infused into the ionization. The ionization methods can be achieved with a single configuration or with separately optimized configurations.

24 Claims, 13 Drawing Sheets

(51) Int. Cl.
*G01N 30/72* (2006.01)
*H01J 49/26* (2006.01)

(56) References Cited

U.S. PATENT DOCUMENTS

| | | | |
|---|---|---|---|
| 5,753,910 A * | 5/1998 | Gourley | H01J 49/24 250/281 |
| 5,788,166 A | 8/1998 | Valaskovic et al. | |
| 6,252,225 B1 * | 6/2001 | Takada et al. | 250/288 |
| 6,297,499 B1 | 10/2001 | Fenn | |
| 6,914,243 B2 | 7/2005 | Sheehan et al. | |
| 6,943,347 B1 | 9/2005 | Willoughby et al. | |
| 7,060,976 B2 | 6/2006 | Sheehan et al. | |
| 7,642,510 B2 * | 1/2010 | McEwen | 250/288 |
| 2002/0020813 A1 * | 2/2002 | Shiokawa | H01J 49/04 250/288 |
| 2005/0035285 A1 | 2/2005 | Tan et al. | |
| 2008/0116370 A1 * | 5/2008 | Splendore et al. | 250/288 |
| 2008/0116371 A1 * | 5/2008 | Wouters et al. | 250/288 |
| 2009/0020696 A1 * | 1/2009 | Bier | 250/288 |
| 2009/0090862 A1 * | 4/2009 | Kawana et al. | 250/288 |
| 2011/0101216 A1 * | 5/2011 | Musselman | 250/282 |
| 2011/0266433 A1 | 11/2011 | Jarrell | |
| 2012/0292526 A1 * | 11/2012 | Hiraoka et al. | 250/423 R |

FOREIGN PATENT DOCUMENTS

| | | | | |
|---|---|---|---|---|
| JP | WO 2011099642 A1 * | 8/2011 | | G01N 27/68 |
| WO | 2006/060130 A2 | 6/2006 | | |
| WO | WO 2011099642 A1 * | 8/2011 | | |
| WO | 2012/031082 A2 | 3/2012 | | |

* cited by examiner

IONIZATION AT INTERMEDIATE PRESSURE FOR ATMOSPHERIC PRESSURE IONIZATION MASS SPECTROMETERS

CROSS-REFERENCE TO RELATED APPLICATIONS

This application is a national stage entry under 35 U.S.C. § 371 of International Patent Application No. PCT/US2013/022883, which was filed on Jan. 24, 2013 claiming priority to U.S. Provisional Patent Application No. 61/591,041, filed Jan. 26, 2012, U.S. Provisional Patent Application No. 61/591,049, filed Jan. 26, 2012, U.S. Provisional Patent Application No. 61/642,871 filed May 4, 2012, and U.S. Provisional Patent Application No. 61/691,029, filed Aug. 20, 2012, the entireties of which are herein incorporated by reference.

FIELD OF DISCLOSURE

The disclosed system and method relate to mass spectrometry. More particularly, the disclosed system and method relate to an intermediate pressure ionization region for linking a first pressure region with a second pressure region of a mass analyzer where the first pressure region is at or near atmospheric pressure.

BACKGROUND

As used herein, the term GC/MS refers to a gas chromatograph ("GC") interfaced to a mass spectrometer ("MS"). The term LC/MS refers to a liquid chromatograph ("LC") interfaced to a mass spectrometer. The current practice in mass spectrometry is to have separate instruments for GC/MS and LC/MS operation. However, at least one manufacturer, Varian, Inc., manufactures a mass spectrometer that can be converted from an atmospheric pressure LC/MS to a vacuum ionization GC/MS by breaking the vacuum and interchanging ion sources.

This approach of converting an LS/MS to a GC/MS is time consuming, requires the breaking of a vacuum, and is only applicable on the specific Varian instrument. Waters and Bruker Corporations offer GC atmospheric pressure ionization mass spectrometer ("API-MS") for instruments designed for LC/API-MS. In these instruments, the effluent from the GC is released into the AP ion source and ionized at AP using an electric discharge. Primarily protonated molecular ions are produced with most fragmentation being from even electron ions and thus are not directly capable of being computer matched to libraries of compounds in common use (e.g., the NIST library) which are generated from odd electron fragmentation using vacuum ionization methods. Thus, identification of unknowns by GC/APMS technology is difficult. However, APMS offers softer ionization with less fragmentation, which makes identification of the quasi molecular ion ([M+H]+, where M represents the molecular weight) easier.

Most currently available atmospheric pressure ionization mass spectrometers ("APIMS") only interface to liquid introduction methods. U.S. Pat. No. 7,642,510 issued to McEwen ("McEwen"), the entirety of which is herein incorporated by reference, discloses an APIMS instrument that can ionize both liquid and gaseous effluents at atmospheric pressure. Typically, primary ions are formed at atmospheric pressure by initiation of a gaseous electrical discharge by an electric field or by electrospray ionization ("ESI") as described in U.S. Pat. No. 6,297,499 issued to Fenn and U.S. Pat. No. 5,788,166 issued to Valaskovic et al., which are also herein incorporated by reference in their entireties. The primary ions in turn ionize the gas phase analyte molecules by either an ion-molecule process as occurs in atmospheric pressure chemical ionization ("APCI"), by a charge transfer process, or by entraining the analyte molecules in a charged droplet of solvent produced in the electrospray process by application of an electric field.

ESI is a method for producing gas phase ions from compounds in solution. In ESI, a liquid is typically forced from a small diameter tube at atmospheric pressure. A spray of fine droplets is generated when an electric potential is applied between the liquid emerging from the tube and a nearby electrode. Charges on the liquid surface cause instability such that droplets break from jets extending from the emerging liquid surface. Evaporation of the droplets leads to a state where the surface charge again becomes sufficiently high (near the Raleigh limit) to cause instability and further smaller droplets are formed. This process proceeds until free ions are generated by either the evaporation process described above or by field emission that occurs when the field strength in the small droplets is sufficiently high for field evaporation of ions to occur. Molecules more basic than the solvent being used in the ESI process are preferentially ionized as are compounds that concentrate at the surface of the droplet. Because ESI generates gas phase ions from a liquid, it is a good ionization method for interfacing LC to MS.

Because ESI is most sensitive and most suitable for basic and polar compounds, most LC/MS instrumentation incorporates an alternative atmospheric pressure ionization ("API") technique called APCI. In APCI, a discharge is generated when a voltage causes electrical breakdown (formation of free electrons and ions) of the surrounding gas. The primary use of this atmospheric pressure ionization method has been as an ionization interface between liquid chromatography and mass spectrometry. This ionization method relies on evaporation of the liquid exiting the liquid chromatograph with subsequent gas phase ionization at atmospheric pressure in a corona discharge.

The primary ions produced in the corona discharge are from the most abundant species—typically nitrogen and oxygen from air or solvent molecules. Regardless of the initial population of ions produced in the corona discharge, diffusion controlled ion-molecule reactions result in a large steady state population of protonated solvent ions. These ions in turn ionize analyte molecules by proton transfer if the reaction is exothermic or by ion addition if the ion-molecule product is stable and infrequently by charge transfer reactions. While this technique tends to be more sensitive than ESI for low molecular weight and less polar compounds, it nevertheless is not sensitive for highly volatile compounds and those less basic than the LC solvent. Thus, neither APCI nor ESI are good ionization methods for a large class of volatile and less polar compounds.

For this reason, other ionization methods, such as photoionization have been applied to LC/MS to more effectively reach a subset of this class of compounds. Photoionization at atmospheric pressure uses an ultraviolet ("UV") source for ionization of gas phase molecules. Typically, a plasma-induced discharge lamp that produces ultraviolet radiation in the range of 100-355 nanometers (nm) is used to generate ionization. Such a source, suitable for use with LC/MS, is available from Synagen Corporation of Tustin, Calif. McEwen (U.S. Pat. No. 7,642,510) discloses that volatile compounds introduced into the atmospheric pressure ion source of an API-MS instrument are more efficiently ionized when a solvent is not present.

Gas chromatographs may be interfaced with mass spectrometers with ion sources operating in a pressure regime near the vacuum of the mass spectrometer. The gas chromatograph is limited to volatile molecules but has higher resolving power for compound separation than LC. The gas chromatograph operates at atmospheric pressure and is interfaced to the mass spectrometry through capillary tubing or a so-called "jet separator", both of which limit the volume of gas entering the vacuum ion source of the mass spectrometer. Gas chromatographs have also been interfaced to API sources as noted above.

So-called "multimode ion sources" are available which combine ESI and APCI for analysis of liquid effluents. Thus, in a single source design, liquid effluents can be ionized by APCI or ESI, but so far not also a gas effluent. No ion source is currently available that can ionize liquid and gaseous effluents from separation devices or solids, liquids, and gases by direct introduction and ionize volatile and nonvolatile high and low mass compounds with a single ionization source.

BRIEF DESCRIPTION OF THE DRAWINGS

The invention will be more fully understood from the following detailed description taken in connection with the accompanying drawings, which form a part of this application and in which.

DETAILED DESCRIPTION

Figure 1:
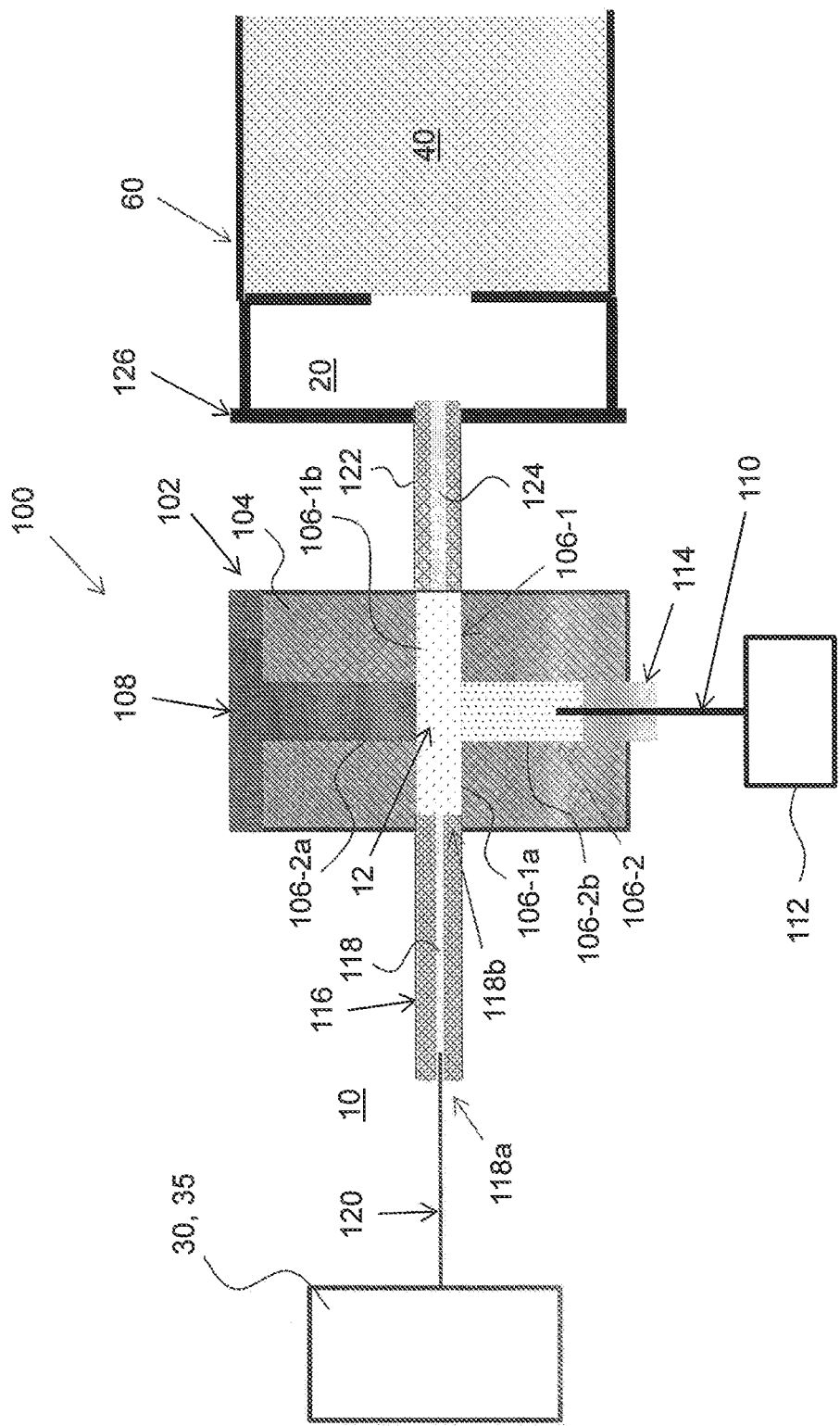
FIG. 1 is a sectional view of an embodiment of an intermediate pressure ionization (IPI) source region with internal holes intersecting.

This description of the exemplary embodiments is intended to be read in connection with the accompanying drawings, which are to be considered part of the entire written description.

In the systems and methods described herein, ionization occurs in the intermediate region between a high pressure input, such as atmosphere pressure, and the low pressure output defined as the first vacuum region of a mass spectrometer. Ionization occurring in a heated intermediate pressure tube separating higher and lower pressure regions were described in International Patent Application No. PCT/US2011/50150. In the disclosed systems and methods, the intermediate pressure ionization region can be heated or cooled to produce ions, application of a voltage to the solution entering the heated intermediate pressure region enhances ionization, linking a first transfer device that receives analyte to a second transfer device with an outlet to the vacuum of the mass spectrometer through an intermediate connector so that the first and second transfer devices are not aligned at 180 degrees to each other improves ionization efficiency, and using such a device in conjunction with an ionizer associated with the connector provides a means of ionization of gaseous effluents into the first transfer region. Thus, the disclosed systems and methods demonstrate improved means of ionization of solutions from, for example, an LC as well as ionization of gases from a GC. Nearly universal ionization is achieved in a single device.

Furthermore, systems and methods are disclosed that enable ionization on any API-MS instrument. The system and method use inlet ionization and enhanced ionization methods, including volatile compounds separated by a GC using alternative ionization methods such as a discharge or photoionization in an intermediate pressure region. Advantages of discharge or photoionization at intermediate pressure using an API-MS instrument includes higher sensitivity, being able to produce computer library searchable mass spectra with electron ionization-like fragmentation, and the advance capabilities often associated with API-MS instruments such as high resolution, accurate mass measurement, and mass selected fragmentation for high sensitivity quantitation.

In some embodiments, a device enables interfacing GCs to commercially available API-MS instruments which are designed to interface to liquid separation methods such an LC or capillary electrophoresis ("CE"). The mass spectrometry apparatus advantageously provides both GC/IP (intermediate pressure) MS and LC/inlet ionization ("II") MS operation on the same instrument. The ionization process for the GC effluent occurs at intermediate pressure using a Townsend or Corona discharge, using photoionization or optionally using alpha or beta emitters from radioactive sources, or electron ionization from a hot wire.

Advantages of GC/IPMS include simple inter-conversion between LC/IIMS and GC/IPMS operation, extended range of compounds that can be analyzed by IPMS by use of a dry purge gas or only the effluent from the GC entering the IP region, higher chromatographic resolution than obtainable with LC/MS, and no vacuum limitation of the GC flow rate allowing faster separations and separation of less volatile compounds. Additionally, intermediate pressure ionization is more sensitive than vacuum electron ionization and APCI MS.

As used herein, a "GC" may be either a commercially available instrument or a specialized instrument for separating compounds in the gas phase. The ionization source described herein advantageously provides a single ionization arrangement that can also be used to ionize compounds irrespective of volatility or mass in a liquid effluent such as from a LC or introduced into the ionization region by infusion. Alternatively, separate interchangeable arrangements can be optimized for liquid and gaseous introduction for ionization, respectively. The arrangement also allows solid, liquid, or gaseous samples to be introduced directly into the ionization region where ions are formed and pass directly into the mass analyzer for mass analysis with high sensitivity. By initiating ionization in the intermediate pressure region between the high pressure, usually AP, and the lower pressure, usually the first vacuum region of a mass spectrometer, ion losses incurred in transferring ions from AP to the vacuum of the mass analyzer are reduced.

API mass spectrometers are capable of ionizing a wide variety of compounds in the effluents from either an LC, a GC, or those introduced directly. In some embodiments in which gaseous effluent is introduced from a GC, the ionization region is closed to atmospheric pressure such that only the effluent from the GC column enters the ionization region.

Referring now to the figures and to FIG. 1 in particular, a sectional view of a system 100 for forming an intermediate pressure ionization ("IPI") source region 12 is illustrated. A connector 102, which may be fabricated from a metal or other heat-tolerant material, may include one or more through holes 106-1, 106-2 (collectively "holes 106") that extend through the body 104 of connector 102 and intersect one another. As shown in FIG. 1, holes 106-1 and 106-2 intersect with one another such that four hole segments or portions 106-1a, 106-1b, 106-2a, and 106-2b are formed. An intermediate ionization region 12 is formed at the intersection between holes 106-1 and 106-2. In some embodiments, such as the embodiment illustrated in FIG. 1, holes 106-1 and 106-2 are formed perpendicular to one another. However, one of ordinary skill in the art will understand that holes 106-1 and 106-2 may be disposed at other angles relative to one another other than right angles.

In some embodiments, connector 102 is heated and portion 106-2a of hole 106-2 receives a removable flange 108 such that portion 106-2a is blocked by a removable flange 108. As will be understood by one of ordinary skill in the art, removable flange 108 can be omitted if hole 106-2 is formed as a blind hole instead of a through hole as illustrated in FIG. 1. In some embodiments, one of holes 106-2a and 106-2b is filled by a removable flange 108. The other portion 106-2b of hole 106-2 receives a discharge needle 110 that is coupled to a power supply 112 (AC or DC) and to an electrical insulator 114, which is received within portion 106-2b to affect ionization. Insulator 114 can be any electrically insulating material including, but not limited to, a ceramic material.

Hole segment 106-1a receives a restricted heated tube 116 that defines an channel 118 that extends through tube 116 such that one end 118a is open to the atmosphere 10 and the other end 118b is open to intermediate ionization region 12. A capillary 120 delivers effluent from a GC 30 or LC 35 to opening 118a defined by heated tube 116. In embodiments where the capillary tube 120 is connected to a GC 30, the tube 116 can heated over its entire length as can be capillary 120. In embodiments where capillary 120 is connected to a liquid induction device, such as an LC, tube 116 can be heated over its entire length, or at least a portion of tube 116 near inlet 118a can be heated. Portion 106-1b of hole 106-1 is coupled to a tube 122 defining a conduit or channel 124. Tube 122 is coupled to flange 126 such that channel 124 is in fluid communication with a first vacuum region 20 of mass analyzer 60, which has a second vacuum region 40. In some embodiments, tubes 116 and 122 are disposed along the same axis defined by hole 106-1 as shown in FIG. 1.

Figure 2:
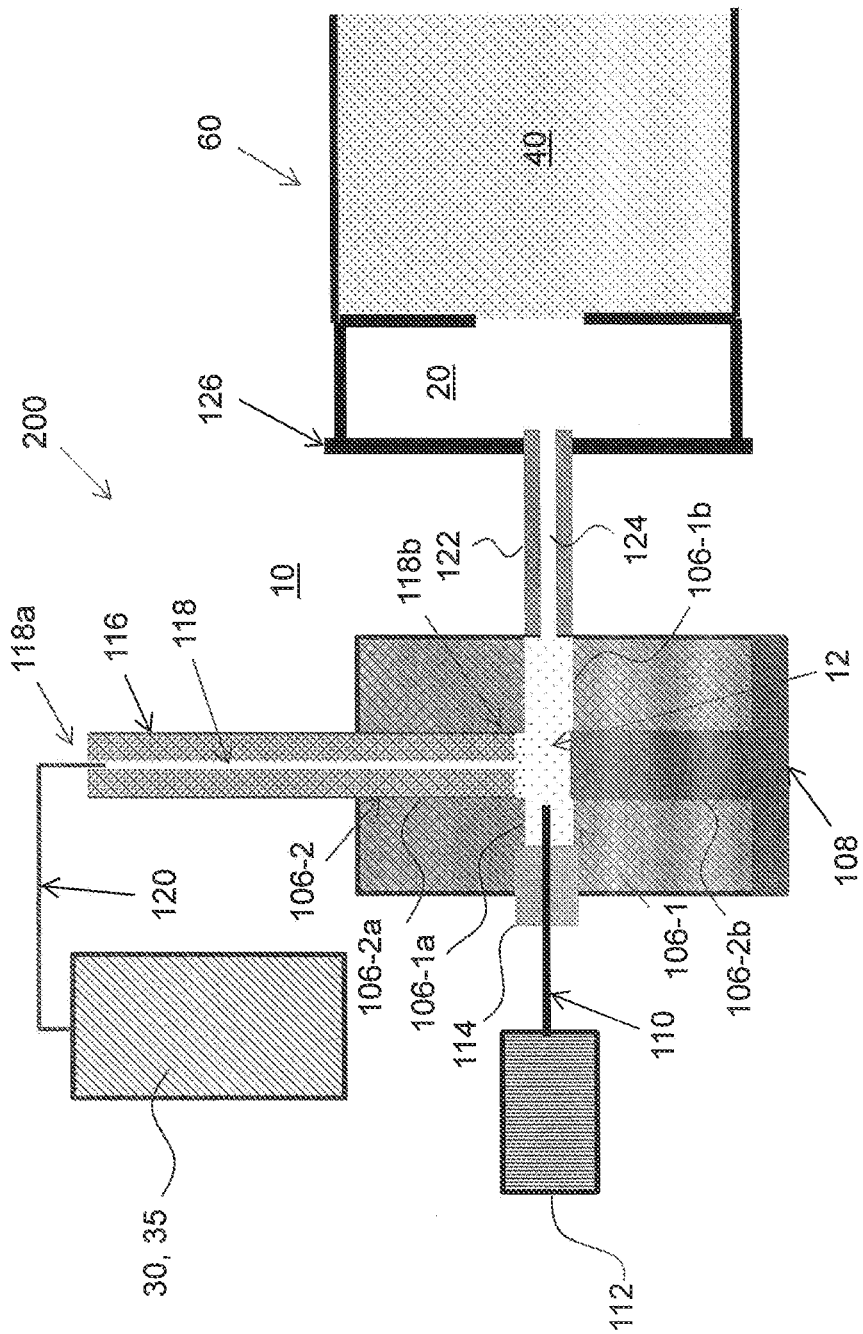
FIG. 2 is another embodiment of an intermediate pressure ionization ("IPI") source region with intersecting internal holes.

The ionization systems can have configurations other than the configuration illustrated in FIG. 1. For example, FIG. 2 illustrates another example of a multi-sectional inlet in which the inlet tubes are coupled to each other such that the tubes are off-axis with one another, i.e., the inlet tubes are not aligned. Gas flowing from the first tube passes through the connector to the second tube. Such arrangements have been shown to be advantageous for inlet ionization methods including, but not limited to, solvent-assisted inlet ionization ("SAII") as described in International Patent Application No. PCT/US2011/50150, the entirety of which is herein incorporated by reference.

As shown in FIG. 2, system 200 includes a connector 102, which is fabricated from a metal or other heat tolerant material. The body 104 of connector 102 defines two or more holes 106-1, 106-2 that extend through body 104 and intersect with one another to form an intermediate ionization region 12.

Portion 106-1a of hole 106-1 extends from intermediate ionization region 12 to the outer surface of body 104 and is sized and configured to receive an insulating material 114 therein. An electrical discharge needle 110, or other electrically conductive device, extends from the intermediate ionization region 12 through insulating material 114 to power supply 112, which is configured to provide discharge needle 110 with an electrical potential. The second portion 106-1b of hole 106-1 is configured to receive a tube 122, which defines a conduit or channel that is in fluid communication with intermediate ionization region 12 and the first vacuum region 20 of mass analyzer 60.

A first portion 106-2a of hole 106-2 extends from the outer surface of body 104 to intermediate ionization region 12 and is sized and configured to receive a tube 116 therein such that a first end 118b of channel 118 is in fluid communication with the intermediate ionization region 12. Another end 118a that is open to the atmosphere 10 and is sized and configured to receive capillary 120 therein. Capillary 120 is coupled to a GC 30 or LC 35.

One of ordinary skill in the art will understand that the inlet tubes may be disposed in other arrangements such that the flow of gas is not linear. Although FIG. 2 illustrates a 90 degree arrangement between the inlet tube 13 and transfer tube 15. In some embodiments, the ionization apparatus comprising needle 110, power supply, and insulator 114 is not required for inlet ionization.

In some embodiments, the second portion 106-2b of hole 106-2 receives a flange 108 for sealing hole portion 106-2b. One of ordinary skill in the art will understand that hole 106-2 can be formed as a blind hole such that flange 108 can be eliminated.

As shown in FIGS. 1 and 2, the heated inlet tube 116 links pressure region 10 and intermediate ionization region 12, which may be at a lower pressure than pressure region 10. From the first pressure region 10 can accept a gas, liquid, or solid sample and introduce the sample to intermediate ionization region 12.

For example, a gas sample can be introduced by a 30 through capillary tube 120 into the heated tube 116 via its channel 118. Ionization of gaseous samples may be induced in the IP ionization region 12 by a discharge using a high voltage (e.g., 1-10 kV) applied to, for example, needle 110 with the voltage being provided by power supply 112. In some embodiment, electron ionization is achieved using a heated wire or metal ribbon, or by photoionization using a photolamp in place of needle 110 and insulator 114. Ions formed within the channel 118 of inlet tube 116 or in the IP ionization region 12 of connector 102 enter the mass analyzer 60 through channel 124 of tube 122 linking the IP ionization region 12 with the first vacuum region 20 of mass analyzer 60. Region 40 may be the vacuum of the mass analyzer 60 and is fluid communication with region 20. One of ordinary skill in the art will understand that tubes 116 and 124 can be incorporated into connector 102 such that the entire arrangement of one piece (i.e., a monolith) of heat tolerant material, which in some embodiment, includes metal.

A liquid sample can be introduced by an LC 35 through capillary tube 120. In some embodiments, the liquid sample includes an analyte in a solvent. Ions can be formed from the analyte by SAII as noted above. Holes 106-2a and 106-2b in FIG. 1 and holes 106-1 and 106-2b in FIG. 2 can be omitted or filled by flanges 108 for SAII operation.

For solid samples, for example, made by incorporating analyte into a matrix, the matrix may be a low molecular weight compound found to produce ions in the inlet ionization through a method called matrix assisted inlet ionization ("MAII"). In MAII, the solid matrix containing analyte prepared by methods that are known by an ordinarily skilled person, may be introduced as a powder or ground crystals directly into inlet tube 116 as described in the aforementioned International Patent Application No. PCT/US2011/50150. In the inlet ionization methods of MAII and SAII, ionization is initiated in the heated inlet tube 116.

Figure 3:
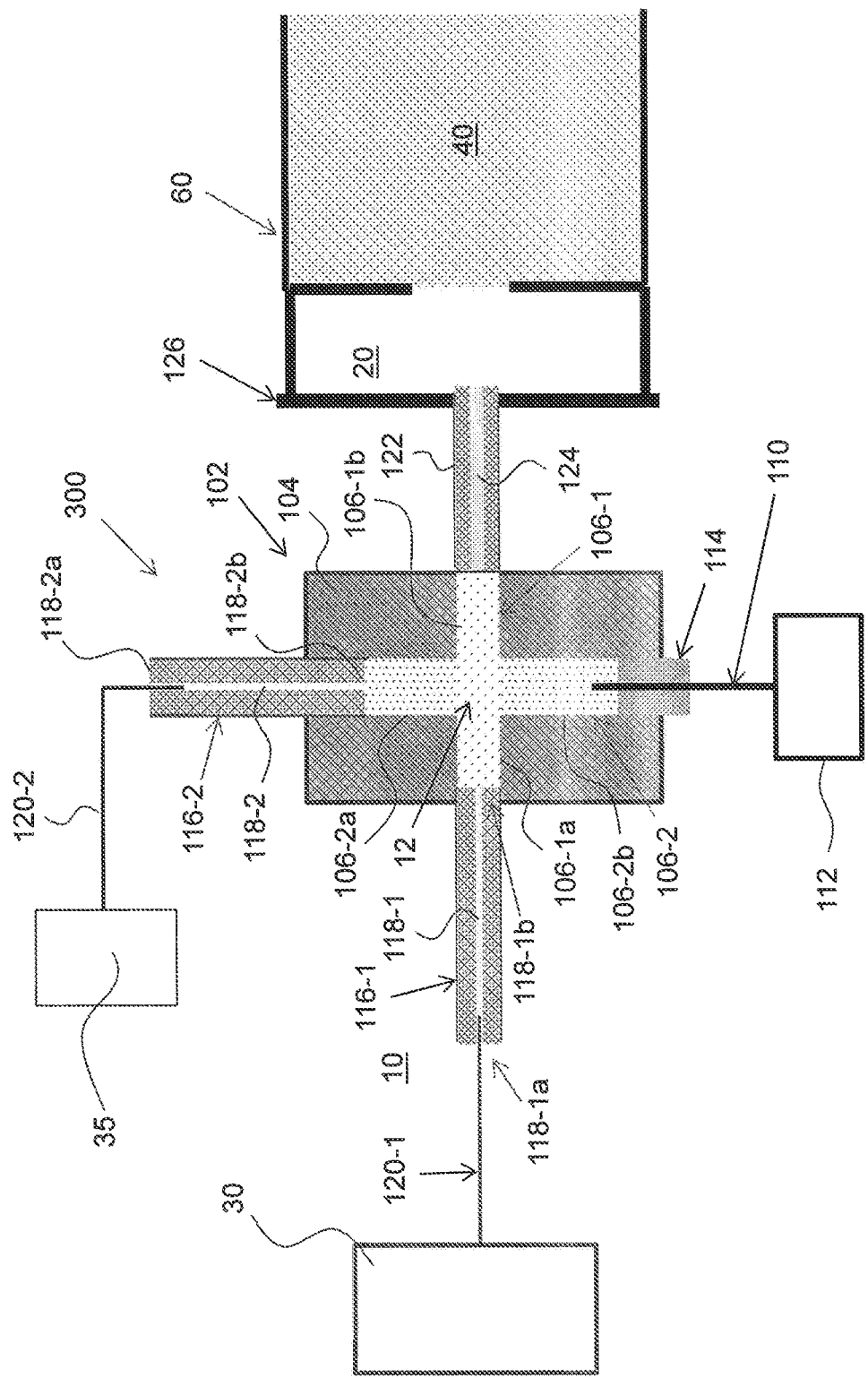
FIG. 3 is another embodiment of an intermediate pressure ionization source region with intersecting internal holes coupled to both a GC and an LC.

As described above, gaseous effluent from a GC 30 can be configured as displayed in FIG. 1 with flange 108 being replaced with a second inlet 116-2 at an angle for tube 116-1 allows simultaneous connection of a GC 30 as shown in FIG. 1 and an LC 30 as shown in FIG. 2. Such an embodiment of a system 300 is illustrated in FIG. 3. As shown in FIG. 3, connector 102 defines first and second through holes 106-1 and 106-2 that intersect with one another within connector 102.

Holes 106-1 and 106-2 intersect with one another such that four hole segments or portions 106-1a, 106-1b, 106-2a, and 106-2b are formed. An intermediate ionization region 12 is formed at the intersection between holes 106-1 and 106-2. In some embodiments, such as the embodiment illustrated in FIG. 3, holes 106-1 and 106-2 are formed perpendicular to one another. However, one of ordinary skill in the art will understand that holes 106-1 and 106-2 may be disposed at other angles relative to one another other than right angles.

Portion 106-1a of hole 106 receives tube 116-1 that defines a channel 118-1 having first and second ends 118-1a, 118-1b. The first end 118-1a of channel 118-1 is disposed in a first pressure area 10, which may be at atmospheric pressure, and receives a first capillary 120-1 therein. Capillary 120-1 is coupled to GC 30. The second end 118-2 of channel 118-1 is disposed within a portion 106-1a of hole 106-1.

LC 35 is coupled to capillary 120-1, which has one end disposed within (or at least within fluid communication with) end 118-2a of channel 118-2 defined by tube 116-2. The second end 118-2b of channel 118-2 is disposed within hole 106-2a of hole 106-2. The other portion 106-2b of hole 106-2 receives a discharge needle 110 that is coupled to a power supply 112 (AC or DC) and to an electrical insulator 114, which is received within portion 106-2b to affect ionization. Insulator 114 can be any electrically insulating material including, but not limited to, a ceramic material.

The GC effluent in such an arrangement enters at 180 degrees relative to tube 116-2 and the LC effluent enters at less than 180 degrees and, in the embodiment illustrated in FIG. 3 at 90 degrees. Tube 116-2 is closed from the high pressure region 10 at the LC inlet when operating the GC and tube 116-1 is closed at the GC inlet when operating the LC so that the higher pressure gas only enters the ionization region 12 from the inlet tube 116-1, 116-2 being used.

The diameter of channels 118-1, 118-2 of tubes 116-1, 116-2 is determined by the gas flow that is desired in the mass analyzer 60 and is dependent on the length of the tubes 116-1, 116-2. In some embodiments, for example, the diameter of channels 118-1, 118-2 is between 0.1 and 1.0 mm. The length of the tubes 116-1, 116-2 can be as short as a skimmer arrangement (e.g., less than or equal to 0.1 mm) or as long as several feet. In some embodiments, tubes 116-1, 116-2 are designed for optimum operation with SAII and MAII with a length between 0.5 cm and 10 cm.

In some embodiments, a GC column may be used as the capillary tube 120. The exit end of the GC column, in some embodiments, may be modified. For example, a GC column may be made of fused silica and have a polyimide coating, which can be a source of contaminant ions that originate from thermal breakdown of the polyimide coating at typical operating temperatures used in the interface between the GC oven and the heated intermediate pressure ionization region 12. Removal of the polyimide coating along a section of the GC column adjacent to the exit end may be performed by either: flame removal; chemical removal by use of liquid acids, bases, or solvents; or by high temperature pre-conditioning of that section of the column for a sufficient time interval. Such removal or pre-conditioning minimizes the observation of contaminant ions in the mass spectrometer and improves the signal to noise. Heating the capillary column 120 to its exit without cool areas maintains the chromatographic resolution for less volatile compounds.

The heat applied to the inlet tube 116 during introduction of an analyte as a gas depends on the volatility of the compounds being analyzed, but typically in the configuration described here will result in a temperature between 100 and 600° C. and more typically 200 and 400° C. For the inlet ionization methods, the inlet tube temperature also varies between ca. 50 and 600° C. and most typically between 250 and 500° C. although cold inlet temperatures between −5 and −80° C. also produces ions for mass spectral analysis.

Reactive gases may also be added to the intermediate pressure ionization region 12 to limit the kinds of compounds that can be ionized by GC/API-MS. For example, addition of ammonia gas allows only compounds more basic than ammonia or those that form stable gas phase ion clusters with $NH_4+$ to be ionized. This can be advantageous when the compounds of interest are highly basic compounds in a matrix of less basic compounds that are not of interest. An example would be ionization of amine containing drugs in, for example, a carbohydrate filler without ionization of oxygen containing compounds.

Alternatively, non-reactive gases such as, for example, dry nitrogen or helium can be added to region 12 to aid charge transfer reactions and formation of odd-electron ions for analyte fragmentation similar to that obtained by electron ionization in vacuum and thus capable of being computer library searched for compound identification.

In matrix assisted inlet ionization, addition of an ammonium salt, such as ammonium tartrate, reduces the background from compounds less basic than ammonia. In SAII, carbonation of the solution being analyzed with $CO_2$ gas reduces background and increases the sensitivity for a variety of compound types including peptides and proteins.

In some embodiments, the first tube 116 is cooled to produce ions from ice particles or other cold solution, and the second tube 122 is heated to desolvate the charged droplets or ice particles produced in the first tube providing bare analyte ions for mass analysis in the mass analyzer 60.

Figure 4:
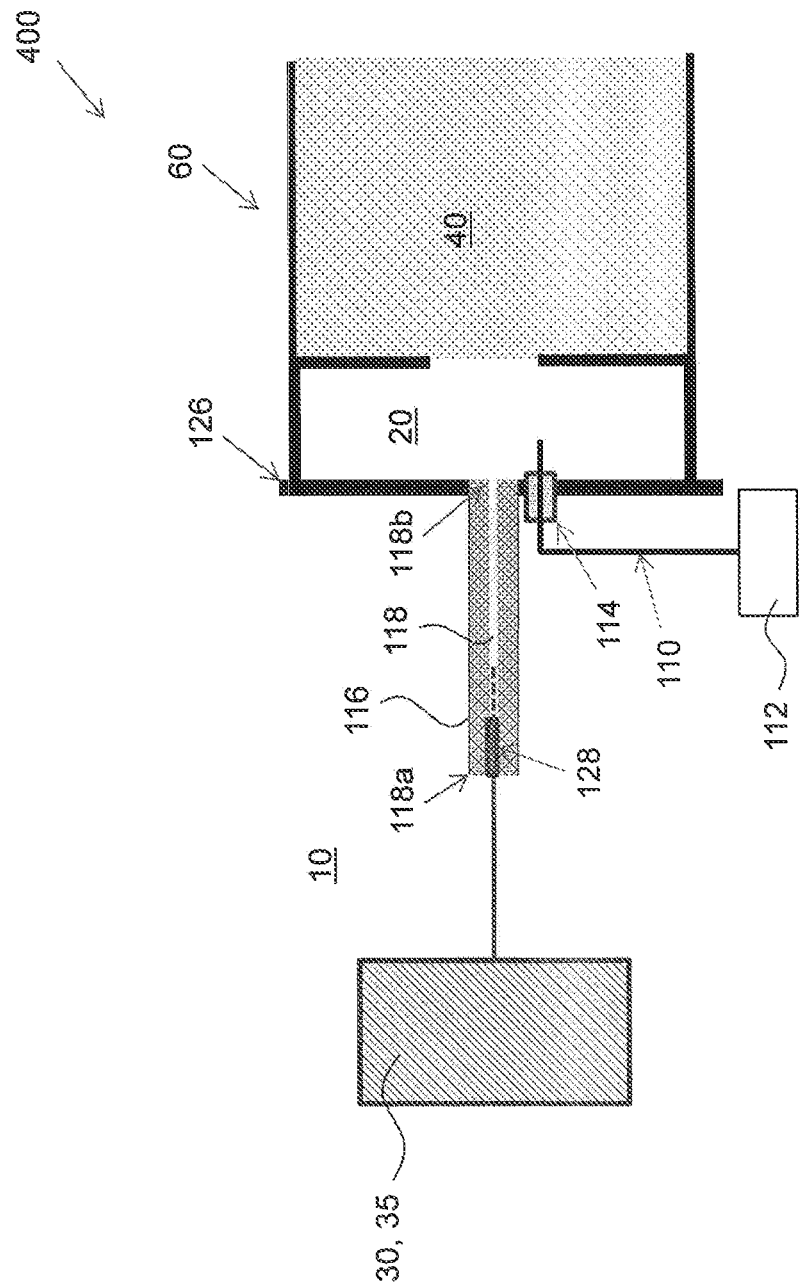
FIG. 4 is a sectional view of another embodiment of an IPI source region which is simplified but requires modification of the ion source of commercial instruments to allow either a discharge adjacent to the exit of the heated inlet capillary, as shown, or a photoionization lamp to affect ionization.

FIG. 4 illustrates another embodiment of a universal IP ion source 400. As shown in FIG. 4, IP ion source system 400 includes a GC 30 or LC 35 coupled to a capillary 120, which has one end disposed within channel 118 of tube 116. In some embodiments, capillary 120 is sealed within channel 118 using a sealant 128 such that channel 118 is sealed from atmosphere 10 and only an effluent from GC 30 enters channel 118.

Channel 118 is coupled to mass analyzer 60 such that channel 118 is in fluid communication with pressure region

20. As described above, pressure region 20 is the first pressure region of mass analyzer 60 and is in fluid communication with region 40. A discharge needle 110 is connected to a high-voltage supply 112, which is used to produce an electric discharge used to create ions from a GC effluent. A portion of needle 110 extends through insulator 114 into vacuum region 20. In some embodiments, insulator 114 is coupled to an opening defined in flange 126 of mass analyzer 60.

The discharge needle 110 is grounded in LC operation and at high voltage with GC operation. Alternatively, a liquid effluent can enter the inlet tube 116 for ionization by SAII. In the event of liquid introduction, the inlet tube 116 is open to the atmosphere with sealant 128 at least partially removed. The discharge region can be electrically isolated from the mass analyzer 60 if necessary by shielding that allows ions to pass through the shielding and into the mass analyzer. The shielding structure may be at or near ground potential.

Figure 5:
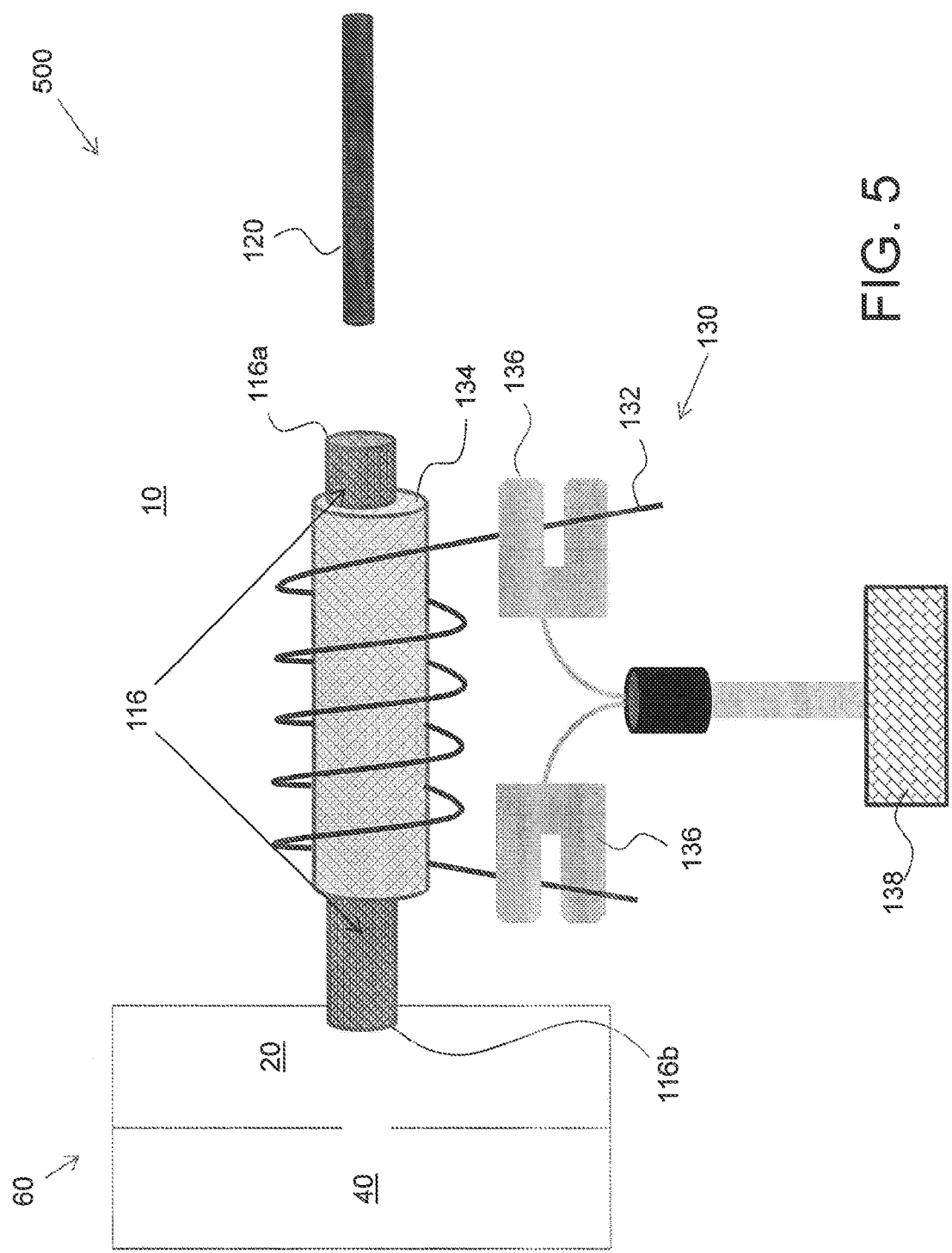
FIG. 5 is a sectional view of another embodiment of an IPI source region showing a heater device.

FIG. 5 is a sectional view of another embodiment of an ionization system 500 for an IP source region showing a single inlet tube 116. In some embodiments, inlet tube 116 is heated by a heater 130 comprising a length of wire 132 wrapped around an insulator 134 disposed on an outer surface of tube 116. Wire 132 is coupled to controller 138 via clamps 136. Controller 138 is configured to adjust the current through wire 132 to achieve a desired temperature for inlet tube 116. While heater 130 is illustrated as a resistive heater comprising a length of wire through which a current runs to heat tube 116, one of ordinary skill in the art will understand that other heaters can be implemented.

Heated tube 116 includes a first end 116a, which is disposed in an area 10 that is at atmospheric pressure. A second end 116b of heated tube 116 is disposed in a low pressure area 20, which may be the first vacuum region of a mass analyzer 60 and in fluid communication with a second low pressure area 40 of mass analyzer 60. A capillary tube 120 can be received within heated tube 116 to introduce an analyte into heated tube 116.

An analyte can be introduced directly, or in a gas or liquid effluent, into a region of sub-atmospheric pressure. In some embodiments, the region is defined by heated tube 116 that links a comparatively high pressure region 10, such as a region at atmospheric pressure, with a low pressure region 20, such as a first vacuum stage of a mass analyzer 60. Analyte ions are formed in tube 116 from a solution by heating or cooling the tube. An electric discharge or other ionization method, such as photoionization, is used at the low pressure end 116b of the inlet tube 116 to produce ions from a gaseous effluent for mass analysis. In this way, all of the sample is introduced into the inlet tube as neutral molecules and subjected to ionization within a confined area.

Ionization enhancement of vaporized analyte occurs at intermediate pressure 20 between the high pressure area 10 at the entrance of the inlet tube 116 and the vacuum of the mass analyzer 40 by application of an electric discharge using for example a needle (not shown in FIG. 5), photoionization using a UV lamp, a radioactive alpha or beta emitter, or an electron beam. The advantage of using a discharge, photoionization, or an electron beam is that they can be turned off by a simple electric switch to allow inlet ionization methods to be applied without any physical change of the source.

In some embodiments, GC/MS is accomplished with the enhanced ionization to ionize vaporized analyte by ion-molecule reactions. Volatile analyte is ionized with the enhanced ionization turned on producing chemical ionization mass spectra. LC/MS is accomplished with the enhanced ionization turned off so that ionization is by solvent assisted inlet ionization. Introduction of any nonvolatile analyte is accomplished using inlet ionization with the enhanced ionization turned off. Improved ionization can be achieved with liquid introduction of volatile and nonvolatile analyte in solution by application of a voltage indirectly to the solution as shown in the embodiment illustrated in FIG. 6 for either DC or AC voltage or directly as shown as shown in the embodiment illustrated in FIG. 7.

Figure 6:
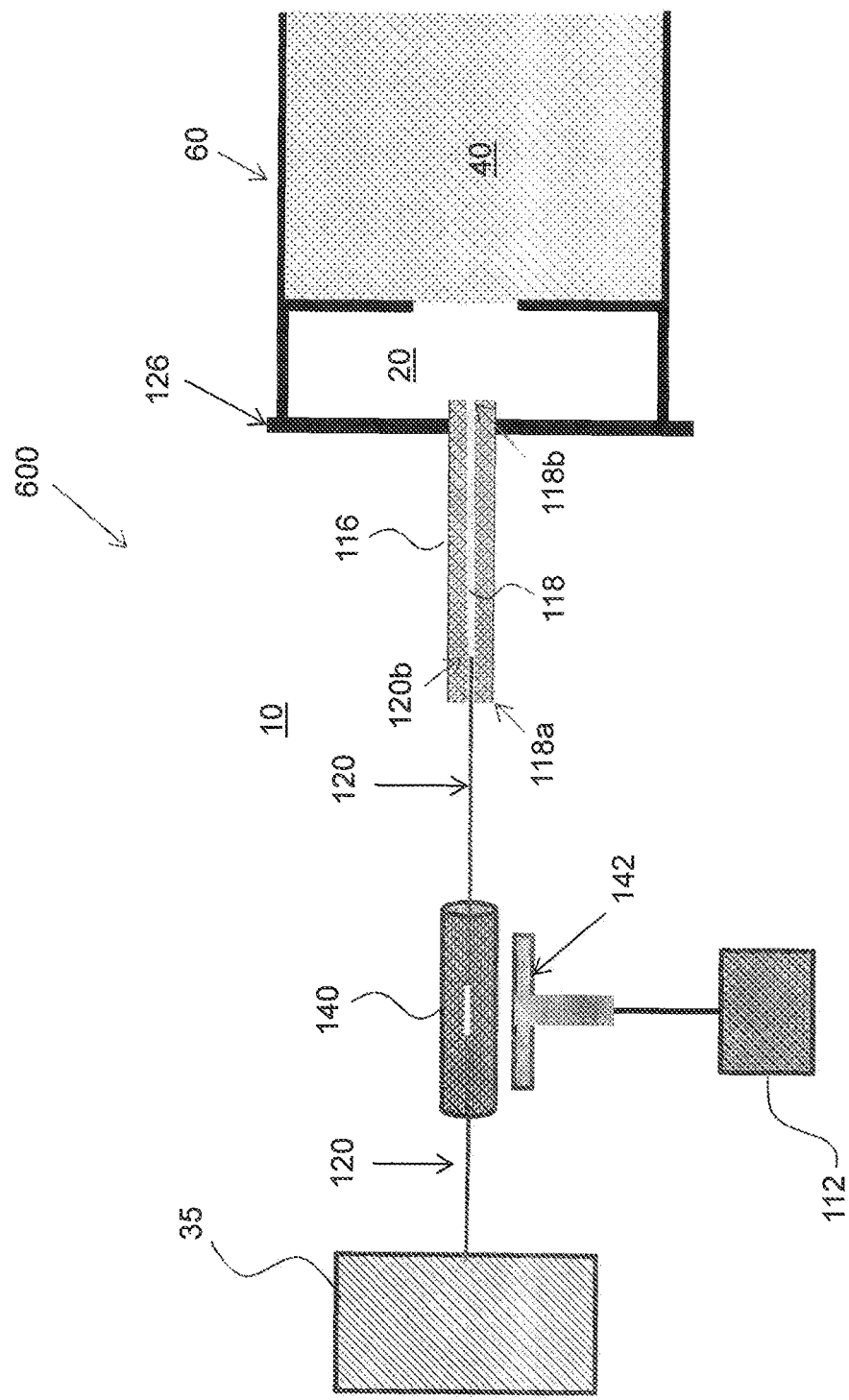
FIG. 6 is a sectional view of another embodiment of an IPI source region and solution delivery device showing voltage inductively applied to a connector.

Referring first to FIG. 6, ionizing system 600 includes an LC 35 coupled to a first capillary tube 120-1, which may be formed from fused silica. A low-dead volume connector comprising a conductive fitting 140 is disposed between and in contact with at least a portion of the first capillary 120-1 and a second capillary 120-2 such that conductive fitting 140 is in fluid contact with capillaries 120-1 and 120-2. In some embodiments, fitting 140 is an LC column. A conductive plate 142 inductively provides the voltage to conductive fitting 140 as conductive plate 142 is not directly in contact with conductive fitting 140. For example, conductive plate 142 may be separated from conductive fitting 140 by an air gap as large as a few millimeters. An insulating material other than air such as, for example, Teflon, can be used to separate conductive fitting 140 and conductive tube 142. In some embodiments, conductive fitting 140 and conductive plate 142 are formed from metal; however, one of ordinary skill in the art will understand that other conductive materials can be used for conductive fitting 140 and conductive plate 142.

Power supply 112, which may be an AC or DC supply, provides the voltage potential to conductive plate 142. In some embodiments, power supply 112 provides a voltage between 100 V and 32 kV, and preferably between 3-10 kV, to conductive plate 142 to enhance ionization within tube 116. In some embodiments, the applied voltage is between 0.5 kV and 3 kV. The applied voltage can be a positive voltage relative to tube 116, which is usually at ground potential, to increase positive ions or can be a negative voltage with respect to tube 116 to increase negative ions.

An end 120-2b of capillary 120-2b is disposed within channel 118 defined by tube 116. A first end of channel 118a is disposed in a first pressure area 10, which is at a higher pressure than area 20 of mass analyzer 60. For example, pressure area 10 can be at atmospheric pressure. The second end 118b of channel 118 defined by tube 116 is disposed in the first vacuum area 20 of mass analyzer 60.

Figure 7:
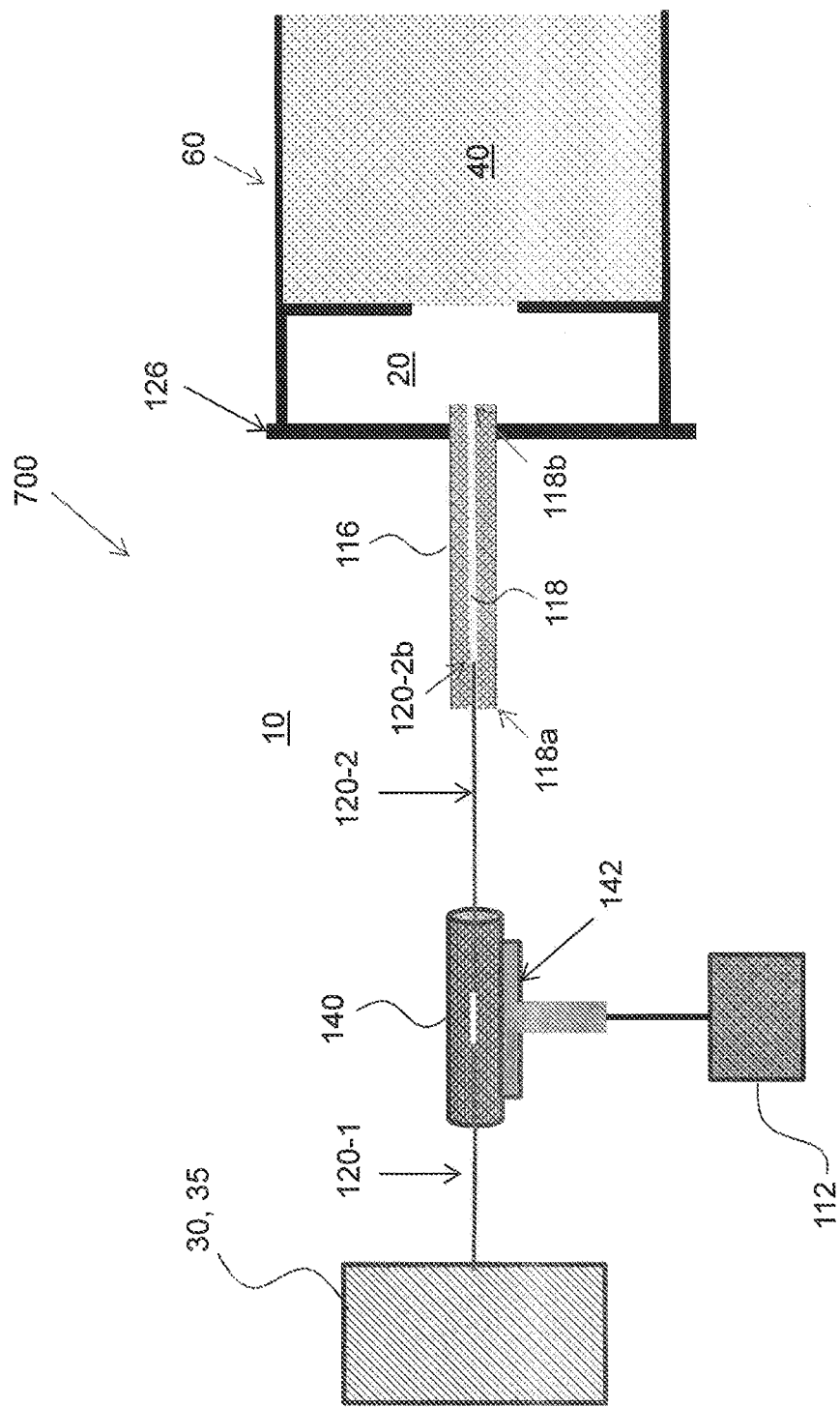
FIG. 7 is a sectional view of another embodiment of an IPI source region an solution delivery device with a voltage directly applied to a connector.

The system 700 illustrated in FIG. 7 is identical to system 600 illustrated in FIG. 6 except that conductive plate 142 is directly in contact with conductive sleeve 140. Repetitive descriptions of the remaining components of system 700 are not provided. In this arrangement, the voltage applied to plate 142 by power supply 112 is preferably between 0.1 and 3 kV. In some embodiments, plate 116 is in direct contact with connector 140 and the connector can be made of non-conduction materials such as a polyetheretherketone (PEEK) polymer or an LC column as commonly used for LC/MS.

In some embodiments, the exit of the fused silica tube 120-2 is disposed outside the channel 118 with a voltage being applied to the solution through the conductive sleeve 140 either indirectly as illustrated in FIG. 6 or indirectly as illustrated in FIG. 7. The fused silica tube 120-2 is disposed within the gas flow caused by the pressure differential that helps direct the solution into the inlet.

The application of a voltage to the conductive fitting 140, either by indirect contact (FIG. 6) or by direct contact (FIG. 7), provides a flow path for the solution from one capillary column 120 to another column 120 and enhances ionization for certain compounds. For example, polyethylene oxides and polypropylene oxides are common contaminants from handling solutions in polymeric containers. Using SAII, ionization is shared between all the contaminant peaks and the analyte of interest. By application of a voltage to the conductive fitting 140, the ion current that is shared with the contaminant is applied to an analyte that is a compound type that accepts the charge such as peptides and proteins. If the fused silica tubing 120-2 delivering solution to the mass analyzer 60 is placed inside the channel 118 defined by tube 116 for optimum SAII, it becomes possible to better observe compounds favored by SAII or those favored by the voltage on method by switching the voltage on or off.

This method of producing ionization enhancement using a voltage applied to a conductive fitting 140 (either directly or indirectly) in combination with a heated channel 118 linking a higher pressure region 10 to a lower pressure region 20 illustrated in FIGS. 6 and 7 provides enhancement at much lower voltage than needed to produce ions using electrospray ionization. In some embodiments, enhancement is achieved when the exit of the fused silica 120 is against or near the hot open channel wall. Using the disclosed systems and methods, a spray is generated by the boiling of the solution as it strikes the hot wall of the channel. Thus, even a low voltage separates charge in the solution and rapid boiling provides charged droplets that evaporate solvent releasing the bare ions inside the channel and measured by the mass spectrometer.

In some embodiments, such as the embodiments illustrated in FIGS. 1-4, volatile analytes introduced by GC are analyzed with the enhanced ionization turned on with added dry nitrogen gas added to the inlet tube 116, for example, to induce fragmentation, or with added water vapor, for example, to reduce fragmentation and only produce protonated molecular ions. In some embodiments, volatile analytes from gaseous introduction are analyzed by using a sealant 128 as illustrated in the embodiment of FIG. 4, such as ceramic to close the high pressure entrance 118*b* of channel 118 defined by tube 116 so that only effluent from the GC column enters the inlet tube 116 thereby affecting ion fragmentation similar to that observed with electron ionization in vacuum instruments in order to allow computer library search methods to identify compounds.

Because ionization occurs at intermediate pressure, ion-ion, ion-electron, and ion-surface collisions which result in neutralization of analyte ions are reduced relative to atmospheric pressure. Further, ionization at atmospheric pressure is accomplished in a larger volume and only a small portion of the analyte ions that are formed are sampled into the inlet of the mass analyzer 60, while in the configuration described herein, all of the ions are produced inside the intermediate pressure region between area 10 and second vacuum region 40 of mass analyzer 60 using instrumentation designed for API-MS.

Additionally, with APCI and ESI, AP ionization methods, a voltage is used and according to Willoughby and Sheehan, ca. 90% of ions entering the MS inlet, when an electric field is present, are lost at the rim of the entrance as described in U.S. Pat. No. 6,943,347, U.S. Pat. No. 6,914,243, and U.S. Pat. No. 7,060,976, the entireties of which are herein incorporated by reference.

The method described herein advantageously enables increasing the scope of compounds that can be analyzed using GC separation by the introduction of a dry, clean purge gas, such as nitrogen, into the ionization region to help exclude air and water or sealing the entrance as described above. Under APCI conditions, there is sufficient water vapor and other organic vapors to cause most of the primary ionization to be in the form of protonated water clusters, protonated solvent, and/or protonated contaminants. The ions formed from protonated water, solvent and/or contaminants, in turn, undergo exothermic, but not endothermic, proton transfer reactions. Thus, compounds more basic than the source of the ionization (water, solvent, or contaminants) are efficiently ionized.

The addition of dry and clean purge gas to the intermediate pressure ionization region, or by sealing the entrance from atmospheric pressure, enables sufficient water and organic contaminants (solvents are not present with GC effluents) to be excluded from the ionization region so that higher energy primary ions become available for ionization of the GC effluent by charge transfer reactions. Thus, for example, charge transfer reactions between the inert gas, such as helium, and the sample can occur, which increases the scope of compounds that can be ionized. Compounds such as napthalene, chlorophenol, diethyleneglycol dimethyl ether, ethyl levulinate (FIG. 8), n-butylsuccinate (FIG. 9), acetophenone (FIG. 10), and other compounds, including those that are not readily ionized under normal APCI conditions, can thus be ionized in the intermediate pressure region.

In addition, compounds that are poorly ionized in liquid APCI or ESI are readily ionized using this methodology, thus increasing the sensitivity of analysis. By excluding contaminants, the sensitivity is improved since ion current from background contaminants is reduced. Further, the high energy charge transfer reactions cause odd-electron fragmentation that is useful in computer generated library identification of unknowns. Alternatively, vapors of solvents such as water or water containing ammonia gas can be added to the intermediate pressure inlet ionization region to reduce the energy of ionization and produce primarily protonated or ammonia adducted protonated analyte ions without significant fragmentation.

Figure 8:
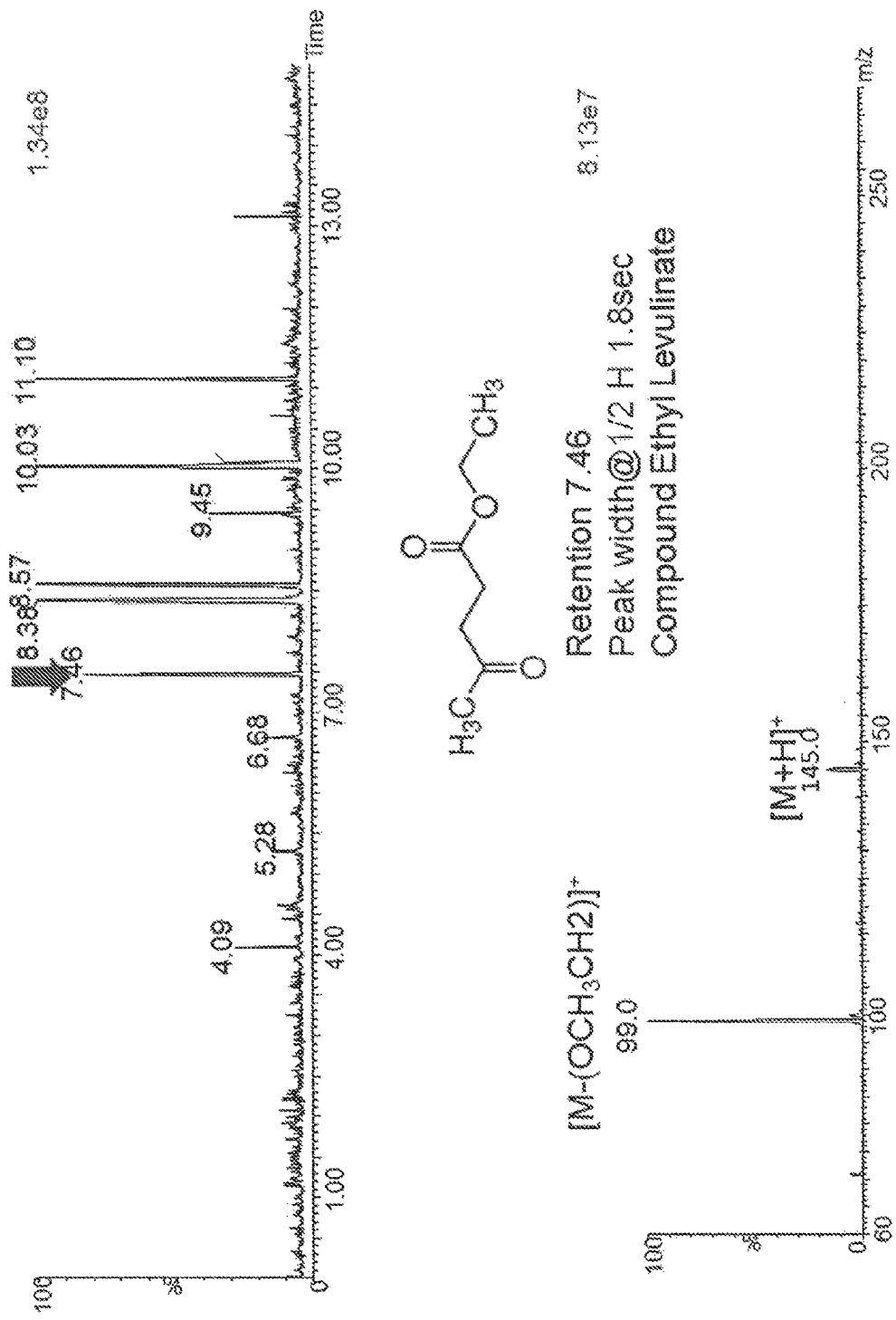
FIGS. 8-10 show results from applications of the arrangements illustrated in FIGS. 1 and 2.
Figure 9:
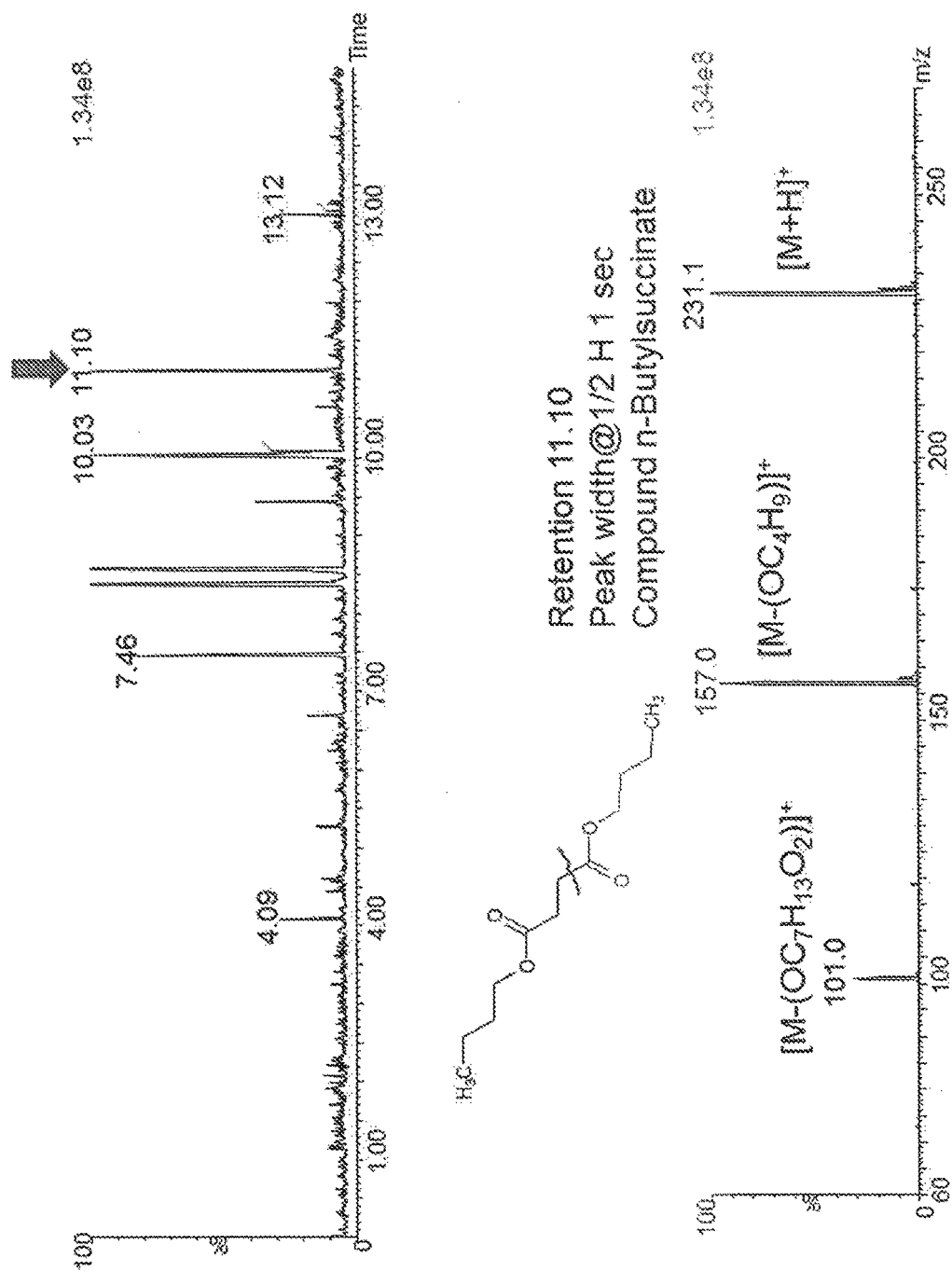

FIG. 8 shows the first example of a mixture of compounds introduced through a gas chromatograph with ionization in the intermediate pressure region by a corona discharge. The upper trace shows the total ion current chromatogram as the compounds elute from the GC column and are ionized in the discharge. The bottom trace shows the mass spectrum of ethyl levulinate. FIG. 9 shows the mass spectrum of n-butylsuccinate from the eluting compound shown by the arrow in the upper trace.

Figure 10:
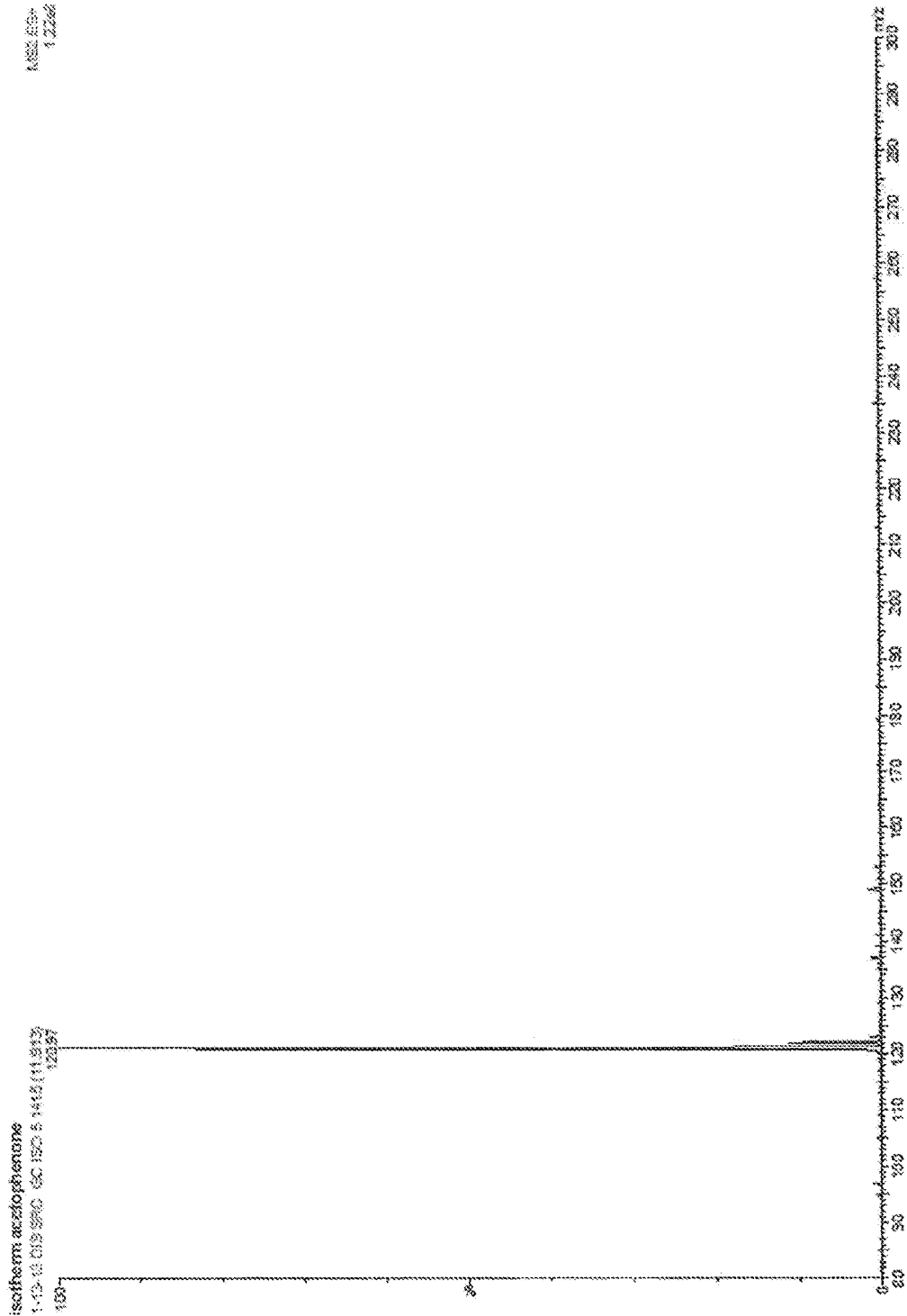

FIG. 10 shows the mass spectrum of an injection of 2 microliters of a 5 parts per billion solution of acetophenone using a device in accordance with FIG. 2.

Figure 11:
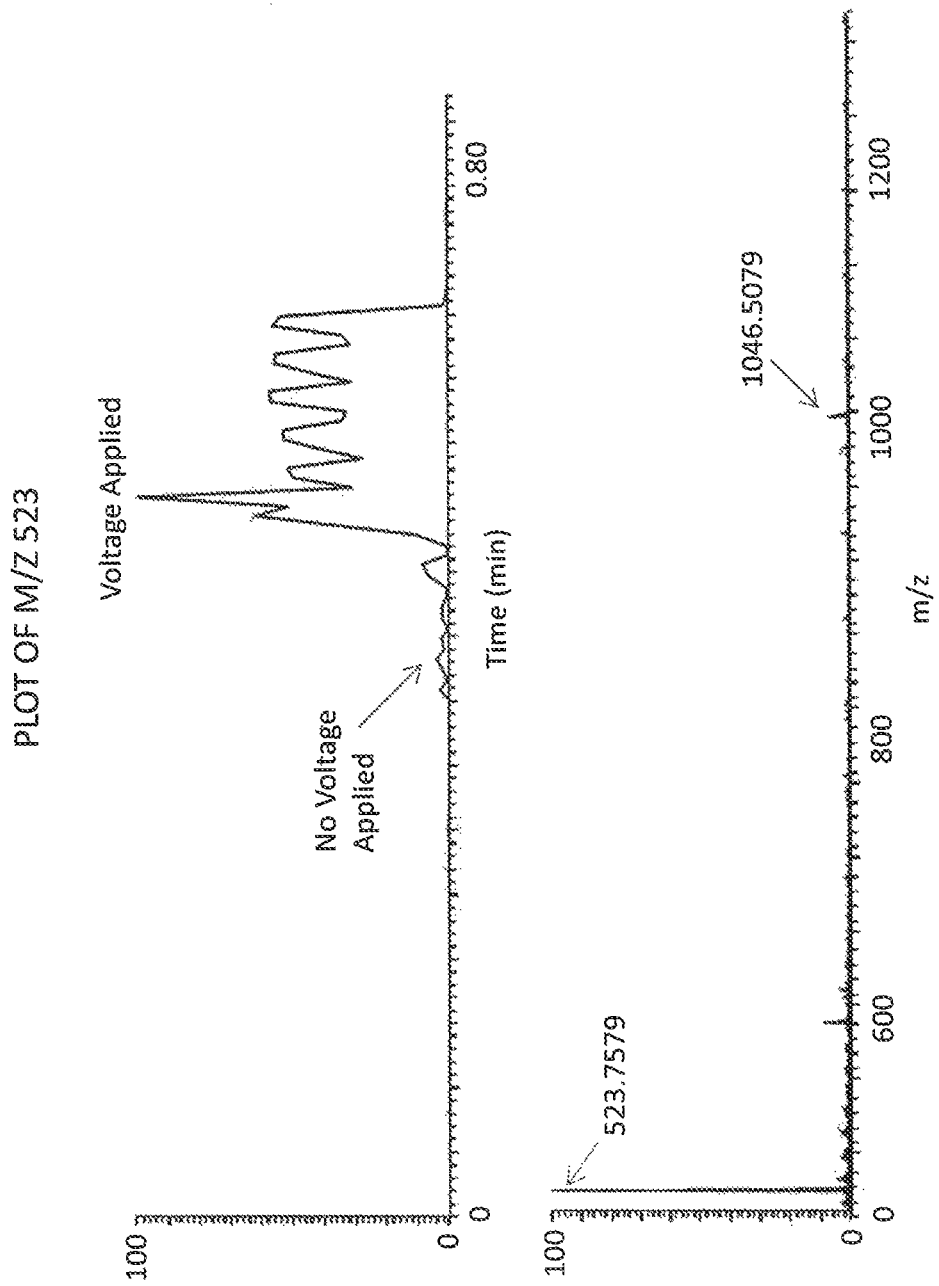
FIGS. 11-12 show results from applications of the arrangement illustrated in FIG. 6.

FIG. 11 is the mass spectrum from 100 femtomoles per microliter of angiotensin II in 1:1 water:acetonitrile with 0.1% formic acid introduced into the inlet tube 116 heated to 400° C. through fused silica tubing 120 at a flow rate of 20 µL/min after passing through the conductive connector 140 shown in FIG. 6 in which 8 kV was placed on the plate 142 with an air gap between it and the connector. In this case, an infusion pump was used to deliver the solution through the conductive connector 140. The trace between 0.4 and 0.5 minutes shows the ion current for the MH2+ ion of angiotensin II with the inlet tube at 500° C. (SAII) and no voltage applied, and the trace between 0.52 and 0.7 minutes show the increased ion current observed with 8 kV is placed on the conductive plate shown below the connector in FIG. 6.

Figure 12:
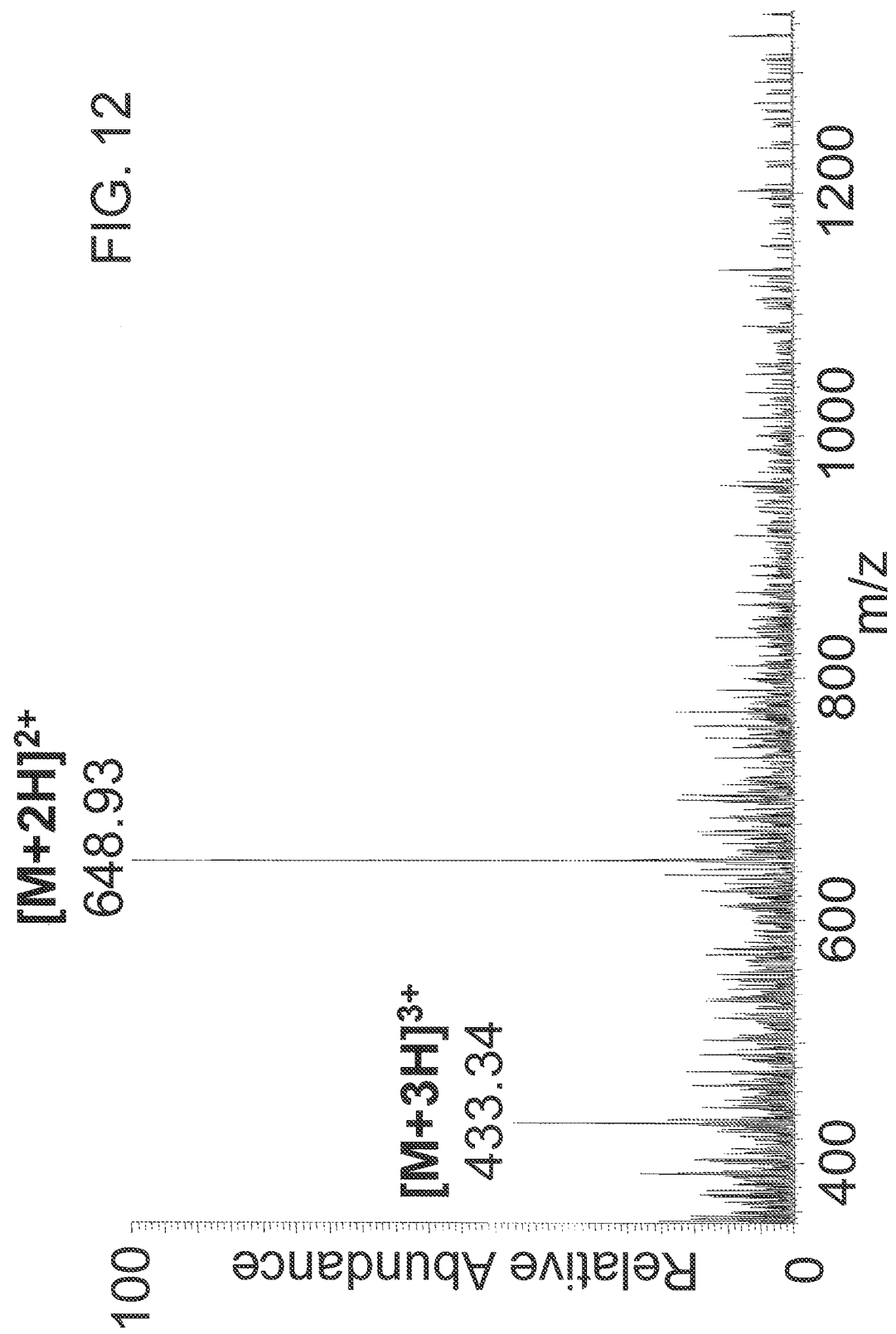

FIG. 12 is an example from a system in accordance with FIG. 1 in which the first inlet tube 116 is at ca. −35° C. and the second inlet 122 is heated to 100° C. The sample is 200 femtomoles per microliter of angiotensin I in water at a flow rate of 12 µL/min. The ion at m/z 648.93 is the doubly charged [M+H2]2+ ion and the ion at m/z 433.34 is the triply charged [M+H3]3+ ion.

Figure 13:
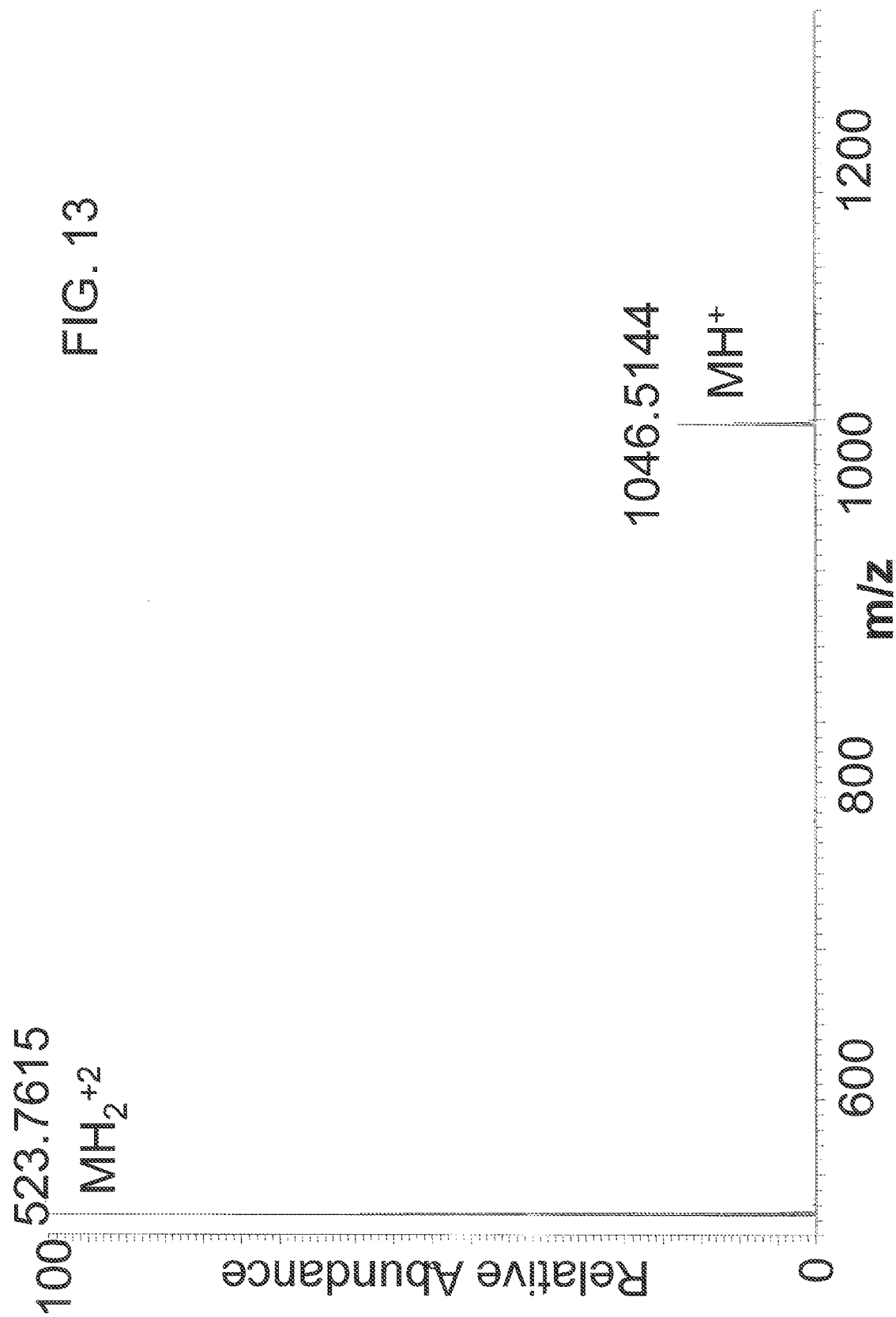
FIG. 13 show results from applications of the arrangement illustrated in FIG. 7 using an AC voltage.

FIG. 13 illustrates the results of applying an AC voltage of 550 V directly to a system 600 in accordance with the embodiment illustrated in FIG. 6. One hundred femtomoles per microliter of angiotensin II was infused at 40 microliters per minute through a fused silica tube 120. The gap between conductive connector 140 and conductive plate 142 was 2 mm. Tube 116 was heated to 375° C. The spectrum illustrated in FIG. 13 was obtained with a one second acquisition.

In some embodiments, the channel is defined as one or more transfer tubes coupled so as to maintain an open channel. Each transfer tube may be coupled to a heating or cooling device such that the transfer tubes are heated or cooled by the heating or cooling device, respectively.

In some embodiments, the tubes comprising the channel are sectioned and coupled together such that the channel in one section is disposed at an angle that is equal to or less than 180 degrees of another adjacent channel. Each section of the channel can be heated or cooled separately.

In some embodiments, the tubes comprising the channel are coupled together by a connector or conductive fitting having a cavity in fluid contact with the channel. The connector including an ionizing device that operates at a reduced pressure relative to atmospheric pressure and causes analyte traveling through the channel to be ionized.

In some embodiments, the tube open to a high pressure region and in fluid contact with the connector includes an ionization device that is sealed from the high pressure region. In some embodiments, a column comprising fused silica tubing provides fluid contact between the effluent from a gas chromatographic column and the interior of the channel such that only the carrier gas and analyte passing through the GC column enter the channel.

In some embodiments, the gas chromatographic column is heated to the entrance of the first tube and at least the first tube and the connector with the ionizing device to which it is connected are heated by a heater.

In some embodiments, the first tube and connector disconnect from the second tube of the channel in such a manner that the vacuum of the mass spectrometer is maintained such that the first tube and connector may be replaced or cleaned without shutting down the instrument.

In some embodiments, liquid effluent from an infusion pump or liquid separation device enters the channel at the opening to the high pressure region, typically through a fused silica capillary.

In some embodiments, the capillary tubing through which solution flows into the open channel is connected to an infusion pump or liquid separation device using a conductive, usually a metal low dead volume, connector through which the flowing solution is in fluid contact. The connector has an air gap of 0.1 to 5 mm between it and a conductor connected to a voltage supply. In some embodiments an insulator, such as a Teflon sheet, is disposed in the air gap between the connector and a plate onto which a voltage of between 1 and 15 kV, preferably 5 to 12 kV, and most preferably between 3 and 10 KV, is imposed relative to the mass spectrometer which is at ground potential.

In some embodiments, a capillary tubing through which solution flows into the open channel is connected to an infusion pump or liquid separation device using a non-conductive, low-dead volume fitting through which the flowing solution is in fluid contact. The connector is placed on a conductive plate that is connected to a voltage supply that applies a voltage to the plate between 0.2 kV and 15 kV, and preferably between 600 and 5 kV and most preferable between 1000 and 4000 V. In some embodiments, the low dead volume connector is formed from a non-conducting material such as, for example, polyetheretherketone or another polymer.

In another embodiment, a capillary tubing through which solution flows into the open channel is connected to an infusion pump or liquid separation device using a conductive low-dead-volume fitting through which the flowing solution is in fluid contact. The connector is attached directly to a voltage supply onto which a voltage between 0.1 and 6 kV, and preferably 0.5 to 3 kV, is applied using either an AC or DC voltage relative to ground potential of the mass spectrometer. In some embodiments, the connector includes an LC column.

The disclosed system and method enable GC/MS or LC/MS analysis to incorporate all of the potential of the mass spectrometers for selected or multiple ion monitoring, for accurate mass measurement, for cone voltage fragmentation, for MS experiments, and the like.

The disclosed system and method also provide several other advantages. For example, since the gaseous or liquid effluent from a preceding separation device enters the confined intermediate pressure ionization region where the analyte is subjected to ionization and mass analysis, the method is highly sensitive. This is in opposition to API sources where ionization occurs in an open atmospheric pressure region as in ESI or APCI, and thus, only a fraction of the ions produced enter the intermediate pressure region for mass analysis.

With the enhanced ionization for gaseous effluents, essentially all of the analyte in a GC effluent can be ionized within the intermediate pressure region with efficient transfer of ions to the mass analyzer producing extremely high sensitivity. The effluent from the GC or from the LC is ionized at intermediate pressure within the same transfer tube, thus facilitating rapid switching between the two separation methods. Alternatively, separate optimized inlet devices can be used for GC and LC separations applying methods that allow rapid switching between the devices when necessary.

Further, direct introduction of analyte into the IP region through a heated transfer tube also produces ions for mass analysis so that the single arrangement described herein is extremely versatile for ionizing a wide variety of compounds using different methods of sample introduction. The disclosed system and method enable chemical compound types to be ionized by GC/IPMS, LC/IPMS, or direct introduction of matrix incorporating analyte so that many chemical compound types can be ionized with high sensitivity.

GC/IPMS also has advantages over GC/vacuum MS. Some of these advantages accrue because GC/IPMS is configured on instruments with atmospheric ionization methods such as APCI and ESI intended for LC/MS operation. Many LC/MS instruments are capable of accurate mass measurement and selected ion fragmentation (i.e., MS/MS) whereas few GC/MS instruments have such capabilities.

The disclosed system and method permit higher linear carrier gas velocity and shorter GC columns, which in turn permits higher boiling compounds to be analyzed. GC/IPMS is not deleteriously affected by high GC carrier gas flow as is GC/vacuum MS since the transfer tube into which the gas effluent enters may be open at the higher pressure region so that the pressure at the vacuum side of the tube does not change significantly. In some embodiments, even when the entrance to the inlet is sealed from atmospheric pressure, the pumping capacitor of the AP ionization instrument is sufficient to allow higher effluent flow rates than can be tolerated in vacuum-based GC/MS ionization instruments.

Additionally, the disclosed systems and methods are capable of producing singly charged ions from volatile as well as some compounds considered nonvolatile including small peptides. The singly charged ions are produced by using the enhanced ionization methods of discharge or photoionization. Larger nonvolatile compounds, such as peptides and proteins, can be ionized with the same arrangement by using inlet ionization rather than the enhanced discharge or photo-ionization. In the intermediate pressure enhanced ionization method with a blanket of dry nitrogen gas or a sealed inlet disclosed herein, even saturated hydrocarbon compounds are ionized, which does not occur with atmospheric pressure ionization.

As an example, GC/IPMS is useful for the analysis of environmental volatile pollutants, synthetic products, off-gas products from polymers and other solid or liquid materials, lipids, fatty acids, alcohols, aldehydes, amines, amino acids, contaminants, drugs, metabolites, esters, ethers, halogenated compounds, certain gases, glycols, isocyanates, ketones, nitrites, nitroaromatics, pesticides, phenols, phosphorus compounds, polymer additives, prostaglandins, steroids, and sulfur compounds.

Although the systems and methods have been described in terms of exemplary embodiments, they are not limited thereto. Rather, the appended claims should be construed broadly, to include other variants and embodiments of the systems and methods, which may be made by those skilled in the art without departing from the scope and range of equivalents of the systems and methods.

What is claimed is:

1. An ionizing system, comprising:
   a first transfer device having a first channel with an inlet disposed in a first pressure region and outlet disposed in a second pressure region having a pressure that is less than a pressure in the first pressure region, the inlet of the first transfer device configured to be a first ionization region for ionizing non-volatile compounds;
   an intermediate coupling device defining a second ionization region for ionizing volatile compounds, the intermediate coupling device configured to receive a portion of the first transfer device and to receive a second transfer device having a second channel that is configured to be coupled to an input of a mass analyzer; and
   a voltage source for applying a voltage prior to the second pressure region,
   wherein the second ionization region is in fluid communication with the first ionization region, the first channel of the first transfer device, and the second channel of the second transfer device.

2. The ionizing system of claim 1, wherein the intermediate transfer device is configured to receive an ionization device therein.

3. The ionizing system of claim 2, wherein the ionization device includes an electrically charged device coupled to a voltage supply.

4. The ionizing system of claim 3, further comprising an electrical insulator coupled to an input of the second channel, the insulator configured to couple the ionization device to the intermediate transfer device to allow independent voltages to be applied to each device.

5. The ionizing system of claim 2, wherein the inlet of the first transfer device is configured to receive a gas or a solution from a heat tolerant conduit.

6. The ionizing system of claim 5, wherein the conduit includes fused silica tubing.

7. The ionizing system of claim 2, wherein the ionizing device includes a wire or ribbon filament onto which a voltage between 10 and 200 V relative to a counter electrode is applied to cause an emission of electrons to effect ionization.

8. The ionizing system of claim 1, wherein the first transfer device is configured to be heated or cooled.

9. The ionizing system of claim 1, wherein the intermediate coupling device is configured to be heated.

10. The ionizing system of claim 1, wherein the second transfer device is configured to be heated.

11. The ionizing system of claim 1, wherein a pressure within the first and second channels defined by the first and second transfer devices, respectively, is between a pressure at the inlet of the first transfer device and a pressure at the input of the mass spectrometer.

12. The ionizing system of claim 1, wherein the first channel defined by the first transfer device is disposed at an angle that is less than or equal to 180 degrees relative to the second channel defined by the second transfer device.

13. The ionizing system of claim 1, wherein the first channel defined by the first transfer device is disposed at an angle between 60 and 120 degrees relative to the second channel defined by the second transfer device.

14. The ionizing system of claim 1, wherein the first channel defined by the first transfer device is disposed at 180 degrees relative to the second channel defined by the second transfer device but is offset within the intermediate connector device such that a line-of-sight is not available between the channels of the first and second transfer device.

15. The ionizing system of claim 2, wherein the ionizing device includes having an edge or a point onto which between ±600 and 10,000 volts are applied to create an electric discharge to initiate ionization.

16. The ionizing system of claim 2, wherein between 1,000 and 4,000 volts are applied to the edge or the point of the ionizing device.

17. The ionizing system of claim 1, wherein the first transfer device, the second transfer device, and the intermediate coupling device are monolithically formed from a heat tolerant material.

18. The ionizing system of claim 1, wherein the intermediate transfer device is in fluid communication with both a gas chromatograph and a liquid chromatograph.

19. The ionizing system of claim 17, further comprising a voltage supply configured to apply a high voltage to an external surface of the intermediate coupling device.

20. The ionizing system of claim 1, further comprising a voltage supply configured to apply a high voltage to an external surface of the intermediate coupling device.

21. An ionizing system, comprising:
   a first conduit defined by a first tube;
   a second conduit defined by a second tube;
   a connector coupling the first tube to the second tube such that the first conduit is in fluid communication with the second conduit by way of the connector the connector, the connector including at least one of a conductive material and a non-conducting material; and
   an ionization region defined by a third tube that is in fluid communication with the second conduit, an opening of the third tube disposed in a first pressure region and a second end of the third tube disposed in a second pressure region having a pressure that is less than a pressure of the first pressure region,
   wherein a voltage of between ±1000 and 16000 volts is applied to a conductive plate that is separated from the connector by an insulating material.

22. The ionizing system of claim 21, wherein a distance between the conductive plate and the insulating material is between 0.1 and 10 mm.

23. The ionizing system of claim 21, wherein the voltage is between ±4000 and 7000 volts.

24. An ionizing system, comprising:
   a first conduit defined by a first tube;
   a second conduit defined by a second tube;

a connector coupling the first tube to the second tube such that the first conduit is in fluid communication with the second conduit by way of the connector;

a power source configured to apply a voltage between ±50 and 7000 volts to the connector; and an ionization region defined by a third tube that is in fluid communication with the second conduit, an opening of the third tube disposed in a first pressure region and a second end of the third tube disposed in a second pressure region having a pressure that is less than a pressure of the first pressure region.

* * * * *